United States Patent
Ebara et al.

(10) Patent No.: US 10,232,321 B2
(45) Date of Patent: Mar. 19, 2019

(54) BLOOD PURIFICATION MEMBRANE, METHOD FOR MANUFACTURING BLOOD PURIFICATION MEMBRANE, AND DIALYSIS DEVICE

(71) Applicant: National Institute for Materials Science, Tsukuba-shi, Ibaraki (JP)

(72) Inventors: Mitsuhiro Ebara, Tsukuba (JP); Koki Namekawa, Tsukuba (JP); Takao Aoyagi, Tsukuba (JP)

(73) Assignee: NATIONAL INSTITUTE FOR MATERIALS SCIENCE, Tsukuba-shi, Ibaraki (JP)

( * ) Notice: Subject to any disclaimer, the term of this patent is extended or adjusted under 35 U.S.C. 154(b) by 110 days.

(21) Appl. No.: 14/913,698

(22) PCT Filed: Aug. 25, 2014

(86) PCT No.: PCT/JP2014/072131
§ 371 (c)(1),
(2) Date: Feb. 23, 2016

(87) PCT Pub. No.: WO2015/029936
PCT Pub. Date: Mar. 5, 2015

(65) Prior Publication Data
US 2016/0199789 A1    Jul. 14, 2016

(30) Foreign Application Priority Data
Aug. 26, 2013 (JP) .................................. 2013-174636

(51) Int. Cl.
*A61M 1/16* (2006.01)
*A61K 35/14* (2015.01)
(Continued)

(52) U.S. Cl.
CPC .......... *B01D 69/148* (2013.01); *B01D 63/04* (2013.01); *B01D 67/0004* (2013.01);
(Continued)

(58) Field of Classification Search
None
See application file for complete search history.

(56) References Cited

U.S. PATENT DOCUMENTS

2004/0178142 A1* 9/2004 Koslow ................. A61L 2/0017
                                                           210/500.29
2007/0213665 A1   9/2007 Curtin et al.
(Continued)

FOREIGN PATENT DOCUMENTS

| EP | 1797850 A1 | 6/2007 |
|---|---|---|
| JP | S55-63652 A | 5/1980 |

(Continued)

OTHER PUBLICATIONS

B. Jha and D.N. Singh, Fly Ash Zeolites, Advanced Structured Materials 78, DOI 10.1007/978-981-10-1404-8_2, Springer Science+Business Media Singapore 2016.*
(Continued)

*Primary Examiner* — Krishnan S Menon
(74) *Attorney, Agent, or Firm* — Drinker Biddle & Reath LLP

(57) ABSTRACT

A blood purification membrane capable of adsorbing creatinine which is a uremic toxin in the blood and purifying the blood, the blood purification membrane including fibers and particles adhered to the aforementioned fibers, wherein the aforementioned fibers are composed of a polymer insoluble in water, the aforementioned particles contain $SiO_2$ and $Al_2O_3$, and pores capable of incorporating at least a portion of the aforementioned uremic toxin are provided in the aforementioned particles.

12 Claims, 11 Drawing Sheets

(51) Int. Cl.
| | |
|---|---|
| *B01D 61/24* | (2006.01) |
| *B01D 63/02* | (2006.01) |
| *B01D 63/04* | (2006.01) |
| *B01D 67/00* | (2006.01) |
| *B01D 69/04* | (2006.01) |
| *B01D 69/08* | (2006.01) |
| *B01D 69/14* | (2006.01) |
| *B01D 71/02* | (2006.01) |
| *B01D 71/26* | (2006.01) |
| *B01D 71/38* | (2006.01) |
| *B01D 71/76* | (2006.01) |
| *B29C 47/00* | (2006.01) |
| *B29K 29/00* | (2006.01) |
| *B29K 31/00* | (2006.01) |
| *B29L 31/00* | (2006.01) |
| *B29L 31/14* | (2006.01) |

(52) U.S. Cl.
CPC ...... *B01D 67/0079* (2013.01); *B29C 47/0014* (2013.01); *A61K 35/14* (2013.01); *A61M 1/16* (2013.01); *B01D 61/243* (2013.01); *B01D 63/02* (2013.01); *B01D 69/04* (2013.01); *B01D 69/08* (2013.01); *B01D 71/028* (2013.01); *B01D 71/26* (2013.01); *B01D 71/38* (2013.01); *B01D 71/76* (2013.01); *B01D 2323/39* (2013.01); *B01D 2325/12* (2013.01); *B29K 2029/04* (2013.01); *B29K 2031/04* (2013.01); *B29L 2031/14* (2013.01); *B29L 2031/731* (2013.01)

(56) References Cited

U.S. PATENT DOCUMENTS

| | | | |
|---|---|---|---|
| 2008/0023394 | A1 | 1/2008 | Naruse et al. |
| 2008/0053891 | A1 | 3/2008 | Koops et al. |
| 2010/0004588 | A1 | 1/2010 | Yeh et al. |
| 2010/0100027 | A1 | 4/2010 | Schilthuizen et al. |
| 2011/0232653 | A1* | 9/2011 | Imashiro ............ A41D 13/1192 128/863 |

FOREIGN PATENT DOCUMENTS

| | | |
|---|---|---|
| JP | 2008-510083 A | 4/2008 |
| JP | 2009-183337 A | 8/2009 |
| JP | 2009-528897 A | 8/2009 |
| JP | 2009-240499 A | 10/2009 |
| JP | 2010-512939 A | 4/2010 |
| JP | A-2010-523311 | 7/2010 |
| JP | 2011-526813 A | 10/2011 |
| JP | A-2012-223254 | 11/2012 |
| JP | A-2012-223674 | 11/2012 |
| WO | WO-2005/102413 A1 | 11/2005 |
| WO | WO 2011/151314 A1 | 12/2011 |

OTHER PUBLICATIONS

Search Report dated Mar. 24, 2017 for European Patent Application No. 14840398.3.

Jiancheng Di et al: "Fabrication of Zeolite Hollow Fibers by Coaxial Electrospinning", Chemistry of Materials, vol. 20, No, 11, Jun. 2008, pp. 3543-3545.

Shigeru Nakai et al., "An overview of regular dialysis treatment in Japan (as of Dec. 31, 2011)," Journal of Japanese Society for Dialysis Therapy, 2013, 46, 1 (including English abstract in front page).

Bonomini M. et al., "Neutrophil Reactive Oxygen Species Production during Hemodialysis: Role of Activated Platelet Adhesion to Neutrophils through P-Selection," Nephron, 1997, 75, 402.

Pertosa G. et al., "Coagulation Cascade Activation Causes CC Chemokine Receptor-2 Gene Expression and Mononuclear Cell Activation in Hemodialysis Patients," J. Am. Soc. Nephrol, 2005, 16, 2477-2486.

Vanholder R. et al., "Review on uremic toxins: Classification, concentration, and interindividual variability," Kidney International, vol. 63, 2003, pp. 1934-1943.

International Search Report dated Oct. 7, 2014 for PCT/JP2014/072131.

Ben et al., "Influence of Si/Al Ratio of ZSM-5 Zeolite on the Properties of Lignin Pyrolysis Products," ACS Sustainable Chernisty & Engineering, vol. 1, pp. 316-324, 2013.

Korobitsyna et al., "Ultra-high-Silica ZSM-5 Zeolites: Synthesis and Properties," Russian Journal of Inorganic Chemistry, vol. 53, No. 2, pp. 169-173, 2008.

JP Office Action dated Aug. 15, 2017 from corresponding Japanese patent application No. 2016-218324 (with attached English-language translation).

* cited by examiner

BLOOD PURIFICATION MEMBRANE, METHOD FOR MANUFACTURING BLOOD PURIFICATION MEMBRANE, AND DIALYSIS DEVICE

TECHNICAL FIELD

The present invention relates to a blood purification membrane, a method for manufacturing a blood purification membrane, and a dialysis device. Priority is claimed on Japanese Patent Application No. 2013-174636, filed Aug. 26, 2013, the content of which is incorporated herein by reference.

BACKGROUND ART

As of 2011, in Japan, the number of patients with chronic renal failure has exceeded 300,000 (Non-Patent Document 1). Among them, only less than a few percent of all patients can receive kidney transplants, and the survival of most patients with renal failure depends on the blood purification method, including hemodialysis.

Hemodialysis requires a large amount (equal to or more than 120 L) of water per patient, and electricity to allow the operation of the equipment. For this reason, fully equipped infrastructure facilities of water and electricity are required for the hemodialysis.

Further, for the dialysis patients, the burden in terms of the number of hospital visits (three times a week), the treatment time (four hours per treatment), and the like in association with the hemodialysis is very heavy. Thus, without a fully operational transportation infrastructure, it is impossible to visit a hospital and receive a dialysis treatment as frequent and as long as described above, which is a problem. Furthermore, similar problems also arise in an emergency where the lifelines are cut off.

Patients with renal failure develop acute uremia when the above-mentioned dialysis treatment is not sufficient. Acute uremia can be dealt with by quickly removing uremic toxins and excess water from the body as an emergency treatment. However, since conventional therapeutic methods for acute uremia involve diffusion and filtration as the main principles, in an environment where the infrastructure and the like are not fully operational, it has been difficult to provide an emergency treatment.

In addition, adsorption columns used in the direct hemoperfusion method or plasma adsorption can selectively eliminate disease-causing substances without requiring a substitution fluid or dialysate. However, the adsorption columns greatly stimulate the blood, and the use of anticoagulant is unavoidable, which has been a problem.

These problems greatly reduce the quality of life (QOL) of dialysis patients.

Based on such a situation, the development of novel medical materials excellent in blood compatibility has been desired which can be used even in an environment where the infrastructure and the like are not fully operational.

It should be noted that there has been a report on excellent blood compatibility of EVAL fibers (blood cell inactivation (Non-Patent Document 2), coagulation system inactivation (Non-Patent Document 3)).

In addition, there are about 100 types of uremic toxins, and of these uremic toxins, creatinine is present in the normal human blood at a concentration of less than 100 μM. However, in the case of dialysis patients, the creatinine level in the blood may become approximately 1,200 μM, and it is required to quickly remove creatinine in particular (Non-Patent Document 4).

CITATION LIST

Non-Patent Documents

[Non-Patent Document 1] Shigeru Nakai et al.: Journal of Japanese Society for Dialysis Therapy 2013, 46, 1
[Non-Patent Document 2] Bonomini M. et al., Nephron, 1997 75, 402
[Non-Patent Document 3] Pertosa G. et al., J. Am. Soc. Nephrol. 2005, 16, 2477-2486
[Non-Patent Document 4] ANHOLDER R. et al., Kidney International, Vol. 63 (2003), pp. 1934-1943

DISCLOSURE OF INVENTION

Technical Problem

The present invention has an object of providing a blood purification membrane that quickly adsorbs a uremic toxin creatinine and is excellent in blood compatibility, a method for manufacturing a blood purification membrane, and a dialysis device.

Solution to Problem

According to a first aspect of the present invention, the blood purification membrane is a blood purification membrane capable of adsorbing creatinine which is a uremic toxin in the blood and purifying the blood, including fibers and particles adhered to the aforementioned fibers, wherein the aforementioned fibers are composed of a polymer insoluble in water, the aforementioned particles contain $SiO_2$ and $Al_2O_3$, and pores capable of incorporating at least a portion of the aforementioned uremic toxin are provided in the aforementioned particles.

According to a second aspect of the present invention, in the blood purification membrane according to the aforementioned first aspect, the $SiO_2/Al_2O_3$ molar ratio of the aforementioned particles may be equal to or more than 18 and equal to or less than 240.

According to a third aspect of the present invention, in the blood purification membrane according to the aforementioned first or second aspect, the aforementioned particles may be zeolite or a zeolite composite.

According to a fourth aspect of the present invention, in the blood purification membrane according to any one of the aforementioned first to third aspects, the aforementioned particles may be particles having a maximum diameter of 5 μm or less.

According to a fifth aspect of the present invention, in the blood purification membrane according to the aforementioned first aspect, the aforementioned polymer may be any one selected from the group consisting of an ethylene-vinyl alcohol copolymer (EVAL), polyvinylpyrrolidone (PVP), polyhydroxyethyl methacrylate (PHEMA), and polyvinyl alcohol (PVA).

According to a sixth aspect of the present invention, in the blood purification membrane according to the aforementioned first aspect, a diameter of the aforementioned fibers may be at least 100 nm and not more than 1,000 nm.

According to a seventh aspect of the present invention, in the blood purification membrane according to any one of the aforementioned first to sixth aspects, the thickness may be equal to or more than 10 nm.

According to an eighth aspect of the present invention, in the blood purification membrane according to any one of the aforementioned first to seventh aspects, the aforementioned particles may be fixed to the aforementioned polymer while the surface thereof is coated with the aforementioned polymer.

According to a ninth aspect of the present invention, a method for manufacturing a blood purification membrane includes a step of dispersing a hydrophilic polymer and particles including $SiO_2$ and $Al_2O_3$ and provided with pores capable of incorporating at least a portion of creatinine serving as a uremic toxin, in a solvent, thereby preparing a dispersion liquid of the particles and the hydrophilic polymer; and a step of producing the blood purification membrane by spinning a yarn from the aforementioned dispersion liquid through an electrospinning method and coagulating the yarn, the blood purification membrane capable of adsorbing creatinine as a uremic toxin in the blood and cleaning blood, which includes fibers and particles adhered to the aforementioned fibers, wherein the aforementioned fibers include a polymer insoluble in water, and contain SiO2 and Al2O3, and the aforementioned particles are provided with pores capable of incorporating at least a portion of the aforementioned uremic toxin.

According to a tenth aspect of the present invention, a dialysis device includes a cylinder, a plurality of thin cylinders filled inside the aforementioned cylinder by aligning the axial direction, a first lid portion for closing the first end side of the aforementioned cylinder, a second lid portion for closing the second end side of the aforementioned cylinder, a first tube joint portion provided in the aforementioned first lid portion, and a second tube joint portion provided in the aforementioned second lid portion, the dialysis device in which an opening of the aforementioned first tube joint portion is in communication with an opening of the aforementioned second tube joint portion only through the inside of the aforementioned plurality of thin cylinders, and the aforementioned thin cylinder is formed by the blood purification membrane according to any one of the aforementioned first to eighth aspects.

According to an eleventh aspect of the present invention, the dialysis device according to the tenth aspect may further include a third tube joint portion provided in the aforementioned cylinder, and a fourth tube joint portion provided in the aforementioned cylinder, in which an opening of the aforementioned third tube joint portion may be in communication with an opening of the aforementioned fourth tube joint portion only through a gap between the inner surface of the aforementioned cylinder and the outer surface of the aforementioned plurality of thin cylinders.

According to a twelfth aspect of the present invention, a dialysis device includes a cylinder, a plurality of thin cylindrical portions formed inside the aforementioned cylinder by aligning the axial direction, a first lid portion for closing the first end side of the aforementioned cylinder, a second lid portion for closing the second end side of the aforementioned cylinder, a first tube joint portion provided in the aforementioned first lid portion, and a second tube joint portion provided in the aforementioned second lid portion, the dialysis device in which an opening of the aforementioned first tube joint portion is in communication with an opening of the aforementioned second tube joint portion only through the inside of the aforementioned plurality of thin cylindrical portions, and the blood purification membrane according to any one of the aforementioned first to eighth aspects is filled between the aforementioned cylinder and the aforementioned plurality of thin cylindrical portions.

Advantageous Effects of Invention

According to the above blood purification membrane, fibers quickly adsorbing a uremic toxin creatinine and exhibiting excellent blood compatibility can be formed.

According to the above method for manufacturing a blood purification membrane, fibers quickly adsorbing uremic toxins and exhibiting excellent blood compatibility can be easily produced within a short period of time.

According to the above dialysis device, by circulating the blood inside the aforementioned plurality of thin cylinders, it is possible to quickly adsorb uremic toxins and to remove uremic toxins from the body without requiring a large amount of water. For this reason, it can be used for an emergency treatment of acute uremia even in sparsely populated areas that are not equipped with sufficient infrastructure, and even in times of emergency where lifelines have been cut off.

According to the above dialysis device, by further allowing water to flow through the gap between the inner surface of the cylinder and outer surface of the thin cylinder and circulating the blood inside the plurality of thin cylinders, it is possible to quickly adsorb uremic toxins and to remove uremic toxins from the body. For this reason, the above dialysis device can be used for the treatment of acute uremia.

The above dialysis device is capable of quickly adsorbing uremic toxins and removing uremic toxins from the body without requiring a large amount of water. For this reason, the above dialysis device can be used for an emergency treatment of acute uremia even in sparsely populated areas that are not equipped with sufficient infrastructure, and even in times of emergency where lifelines have been cut off.

DESCRIPTION OF EMBODIMENTS

In view of the above circumstances, the inventors of the present invention discovered that zeolite having a pore size adapted to the size of creatinine and an $SiO_2/Al_2O_1$ molar ratio of equal to or more than 18 and equal to or less than 240 can selectively adsorb creatinine in the pores, and an EVAL fiber having an average diameter of about 800 nm and excellent in blood compatibility is most suitable in terms of morphology and mechanical strength. Further, the inventors of the present invention found that a composite film formed by fixing the above zeolite to an EVAL fiber can remove uremic toxins from the body without requiring a large amount of water. Furthermore, the inventors of the present invention found that it may become a novel medical material that can be used for an emergency treatment of acute uremia by adsorbing and removing creatinine, even in sparsely populated areas that are not equipped with sufficient infrastructure, and even in times of emergency where lifelines have been cut off, thereby completing the present invention. The present invention includes the following configurations.

First Embodiment

Hereinafter, a blood purification membrane, the manufacturing method thereof and the dialysis device according to the first embodiment of the present invention will be described with reference to the accompanying drawings.

<Dialysis Device>

First, the dialysis device (dialyzer) according to the first embodiment will be described.

Figure 1:
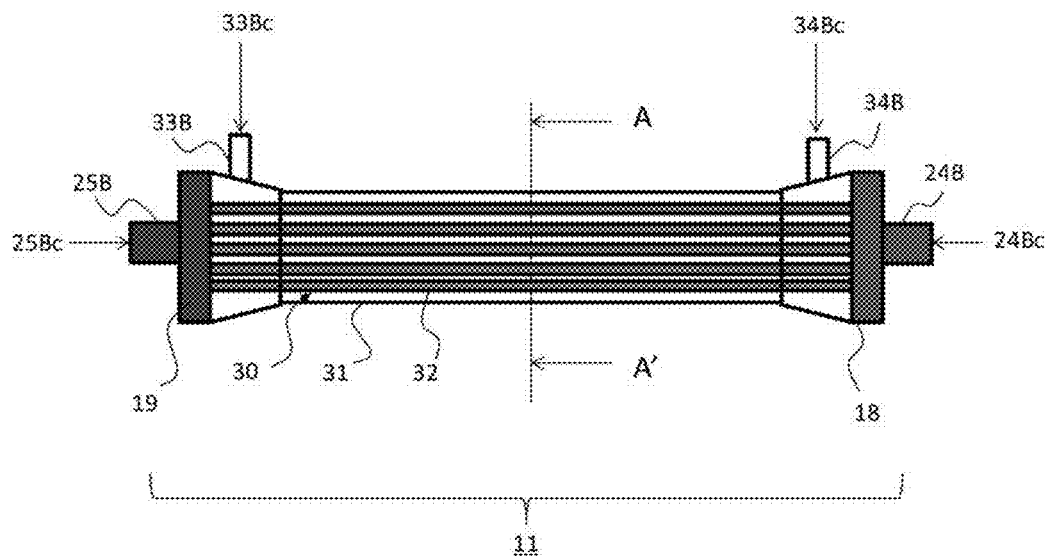
FIG. 1 is a schematic diagram showing an example of a dialysis device according to a first embodiment of the present invention.
Figure 2A:
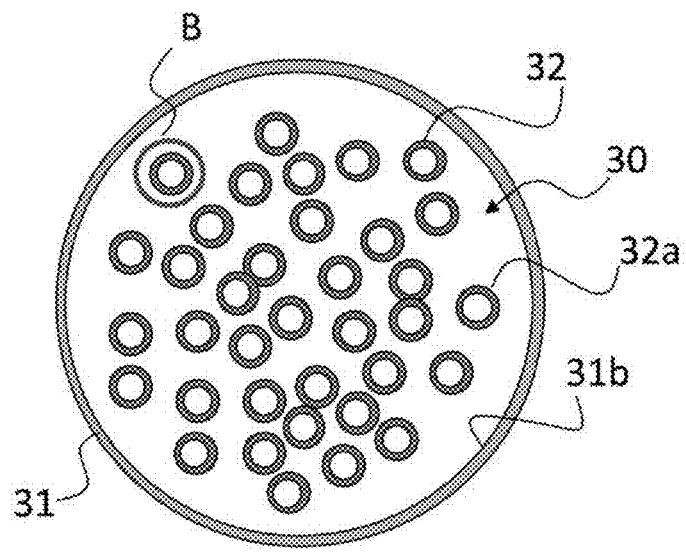
FIG. 2A is a cross sectional view taken along the line A-A' in FIG. 1.
Figure 2B:
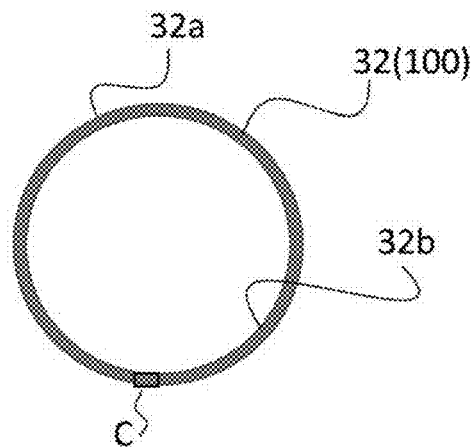
FIG. 2B is an enlarged view of a portion B in FIG. 2A.
Figure 2C:
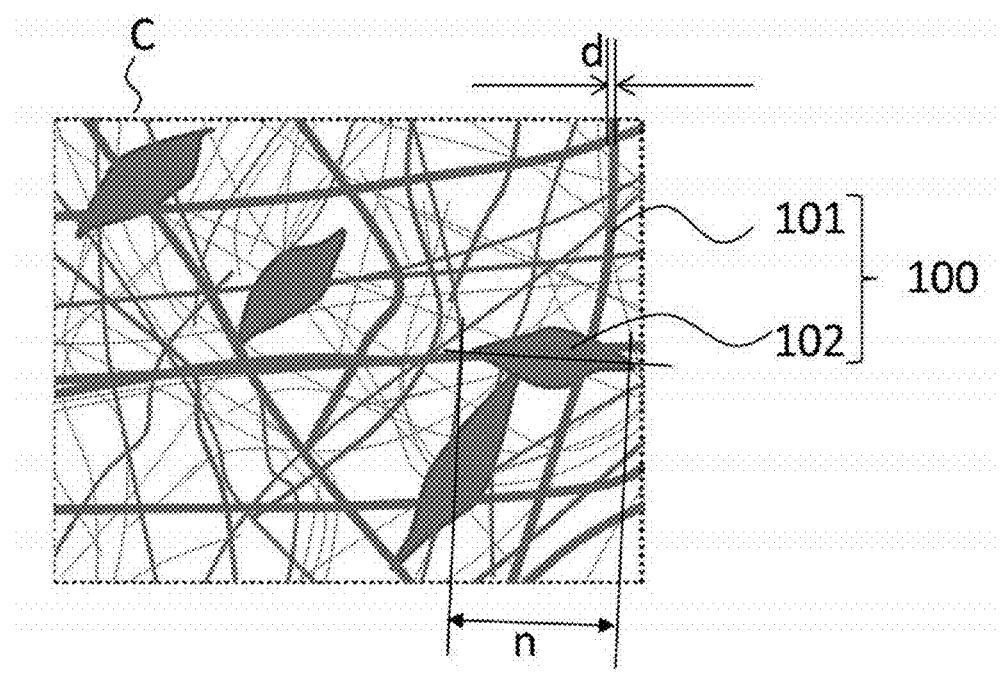
FIG. 2C is an enlarged view of a portion C in FIG. 2B.

FIG. 1 is a schematic diagram showing an example of the dialysis device according to the first embodiment. FIG. 2A is a cross sectional view taken along the plane A (line A-A') in FIG. 1. FIG. 2B is an enlarged view of a portion B in FIG. 2A. FIG. 2C is an enlarged view of a portion C in FIG. 2B.

As shown in FIG. 1, a dialysis device 11 is mainly configured by including a cylinder 31, a plurality of thin cylinders 32, a first lid portion 18, and a second lid portion 19. The plurality of thin cylinders 32 are loaded in the cylinder 31 by aligning the axial direction. The first lid portion 18 closes the first end side of the cylinder 31. The second lid portion 19 closes the second end (other end) side of the cylinder 31.

A first tube joint portion 24B is provided in the first lid portion 18. A second tube joint portion 25B is provided in the second lid portion 19.

In addition, a third tube joint portion 33B is provided on the second end side of the cylinder 31, and a fourth tube joint portion 34B is provided on the first end side of the cylinder 31.

An opening 24Bc of the first tube joint portion 24B is in communication with an opening 25Bc of the second tube joint portion 25B only through the inside of the plurality of thin cylinders (dialysis membrane) 32 (not shown).

In addition, a third opening 33Bc of the third tube joint portion 33B is in communication with an opening 34Bc of the fourth tube joint portion 34B only through a gap 30 between an inner surface 31b of the cylinder 31 and an outer surface 32a of the plurality of thin cylinders 32 (not shown).

In the present embodiment, as shown in FIG. 2A, 38 thin cylinders 32 are placed in a single cylinder 31. However, the number of the thin cylinders 32 is not limited thereto, and 10 to 100,000 of thin cylinders 32 may be placed in one cylinder 31. Typically, depending on the diameter of the thin cylinders 32, the number of the thin cylinders 32 placed in a single cylinder 31 is about 10,000.

In the present embodiment, as shown in FIG. 2B, the thin cylinders 32 are cylinders with an outer surface 32a and a cylindrical inner surface 32b, and having a substantially circular outer shape in cross-sectional view in a direction perpendicular to the axial direction. However, the outer shape of the thin cylinders 32 is not limited thereto, and may be formed into a polygonal shape.

As shown in FIG. 2B, the thin cylinders 32 are formed by the blood purification membrane 100 according to the present embodiment.

The blood purification membrane 100 is cut into a predetermined size, wound into a roll, and the superimposed portions are bonded to form the thin cylinders. Thereby, it is possible to form the thin cylinders 32 constituted of the blood purification membrane 100.

The thin cylinders 32 constituted of the blood purification membrane 100 can also be formed by forming the blood purification membrane 100 into a substantially cylindrical shape, followed by hollowing out a cylindrical part of the central portion in the axial direction.

In addition, the thin cylinders 32 constituted of the blood purification membrane 100 can also be formed by accumulating fibers so as to wind around a cylindrical member and then removing the cylindrical member in the spinning step.

<Blood Purification Membrane>

The blood purification membrane 100 according to the present embodiment is configured by aggregating and accumulating fibers for blood purification in the present embodiment. The blood purification membrane 100 according to the present embodiment is a blood purification membrane capable of adsorbing the uremic toxin creatinine in the blood and cleansing the blood.

Creatinine is a uremic toxin having a structure shown in the following formula (1) and has a size that can be enclosed by a rectangular parallelepiped having a size of X=0.71 nm, Y=0.80 nm, and Z=0.30 nm, which is the smallest rectangular parallelepiped to enclose creatinine. Although the creatinine concentration in the normal human blood is less than 100 μM the creatinine concentration in the blood may become about 1,200 μM in the cases of dialysis patients.

[Chemical Formula 1]

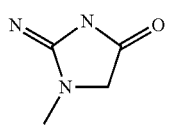

(1)

As shown in FIG. 2C, the blood purification membrane 100 according to the present embodiment is composed of fibers 101 and particle 102 deposited to the fibers 101.

The fibers 101 are composed of a polymer insoluble in water.

The fibers 101 may be composed of for example, a hydrophilic polymer insoluble in water. Examples of the materials of the hydrophilic polymer include, in addition to ethylene-vinyl alcohol copolymers (EVAL) shown in the following formula (2), polyvinylpyrrolidone (PVP), polyhydroxyethyl methacrylate (PHEMA), and polyvinyl alcohol (PVA), and they are used by performing an insolubilization treatment such as crosslinking. In particular, EVAL is suitably used as a material for the hydrophilic polymer since the insolubilization treatment is not required.

[Chemical Formula 2]

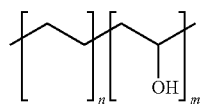

(2)

A diameter d of the fiber 101 is preferably equal to or greater than 100 nm and equal to or less than 1,000 nm. As a result, when forming a membrane, it is possible to form a mesh-like membrane in which numerous fine pores are present, and it is possible to move uremic toxins in the blood quickly into the membrane and to make pores 102a of the particle 102 present in arbitrary locations within the membrane to capture the uremic toxins.

The particle 102 contains $SiO_2$ and $Al_2O_3$ and provided with the pores 102a is capable of capturing at least a portion of creatinine as a uremic toxin.

The size of the pores 102a of the particle 102 is preferably at least 1.39 times, 5 but not more than 2.14 times, as large as the area of the smallest surface of the smallest rectangular parallelepiped enclosing the uremic toxin in the form of creatinine. As a result, it is possible to capture at least a portion of creatinine within the pores 102a in a stable manner.

The hydrophilicity/hydrophobicity ($SiO_2/Al_2O_3$ molar ratio) of the particle 102 is preferably equal to or greater than 18 and equal to or less than 240. As a result, a portion of creatinine incorporated within the pores 102a can be held in a stable manner.

A diameter n of the particle 102 is preferably equal to or less than the maximum diameter, which is 5 μm. As a result, it is possible to produce the blood purification membrane 100 in which the particle 102 is uniformly dispersed in the fibers 101.

Examples of the material of the particle 102 include zeolite or zeolite composites. Examples of the zeolite composites include composites of zeolite and metal organic structures. In the metal organic structures, any metal may be used as the metal species. By synthesizing a structure using an organic linker having a diameter substantially equal to the diameter of creatinine, it is possible to synthesize a metal organic structure that is capable of capturing at least a portion of creatinine in the pores. More specifically, 2,6-Naphthalene dicarboxylic acid and the like are preferred.

Figure 3:
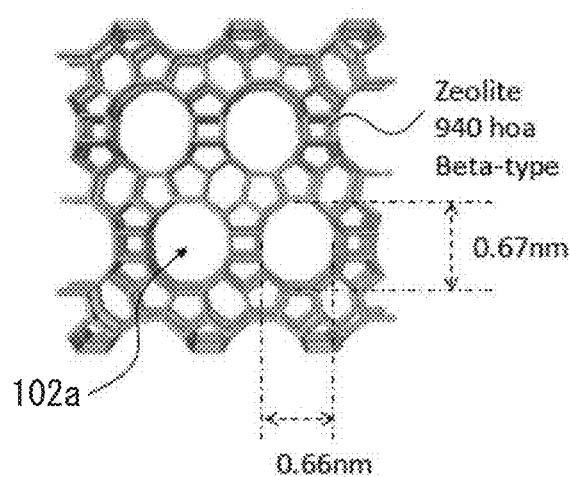
FIG. 3 is an enlarged view of a partial structure of HSZ-940HOA, which is a zeolite (Beta-type).

FIG. 3 is an enlarged view of a partial structure of the beta type zeolite HSZ-940HOA.

As shown in FIG. 3, the beta type zeolite includes the pores 102a with an opening area of 0.66 nm×0.67 nm. Because of the following relationship: the size of the pores 102a ($nm^2$)/the minimum area of the rectangular parallelepiped enclosing creatinine ($nm^2$)=2.07 ($nm^2$), the size of the pores 102a of the particle 102 is at least 1.39 times, but not more than 2.14 times, as large as the area of the smallest surface of the smallest rectangular parallelepiped enclosing the uremic toxin in the form of creatinine. As a result, the beta type zeolite can incorporate at least a portion of creatinine within the pores 102a.

FIG. 3 is an enlarged view of a partial structure of the beta type zeolite HSZ-940HOA.

As shown in FIG. 3, the beta type zeolite includes the pores 102a with an opening area of 0.66 nm×0.67 nm. Because of the following relationship: the size of the pores 102a ($nm^2$)/the minimum area of the rectangular parallelepiped enclosing creatinine ($nm^2$)=2.07 ($nm^2$), the size of the pores 102a of the particles 102 is at least 1.39 times, but not more than 2.14 times, as large as the area of the smallest surface of the smallest rectangular parallelepiped enclosing the uremic toxin in the form of creatinine. As a result, the beta type zeolite can incorporate at least a portion of creatinine within the pores 102a.

In addition, it is preferable because the beta type zeolite having a composition that satisfies the $SiO_2/Al_2O_3$ molar ratio of equal to or greater than 18 and equal to or less than 240 exhibits moderate hydrophilicity and hydrophobicity, and can firmly adsorb at least a portion of creatinine within the pores 102a.

Figure 4:
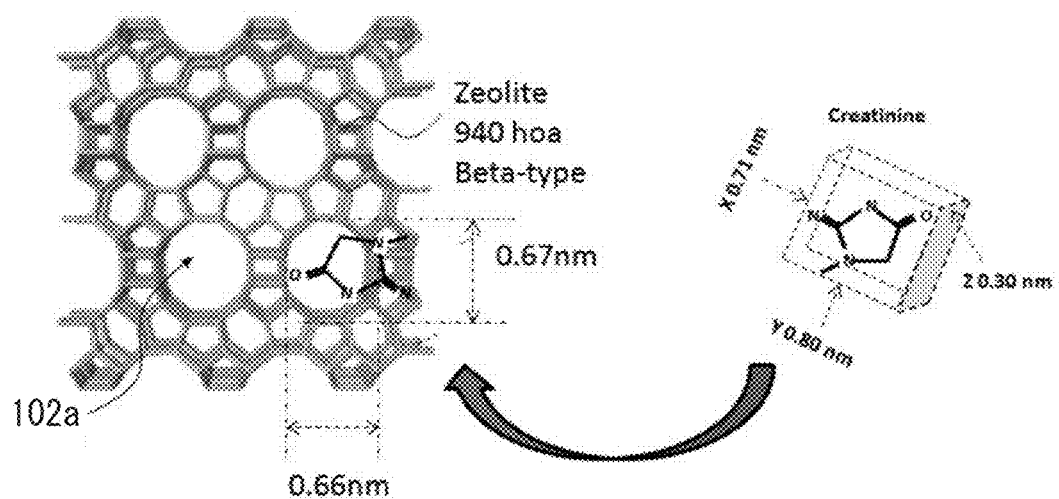
FIG. 4 is a diagram showing an example of a state in which a portion of creatinine is stably retained in the pore.

FIG. 4 is a diagram showing an example of a state in which a portion of creatinine is stably retained within the pores 102a. The article 102 is preferably fixed to the hydrophilic polymer. As a result, the blood purification membrane 100 can be made into a membrane which is excellent in blood compatibility and holds the particle 102 in a stable manner.

With the above configuration, the particle 102 is configured in such a manner that at least a portion of creatinine can be incorporated into the pores 102a and the incorporated portion can be held stably.

<Method for Manufacturing Blood Purification Membrane>

The method for manufacturing a blood purification fiber according to the present embodiment includes a dispersion liquid preparation step S1 and a membrane formation step S2.

The dispersion liquid preparation step S1 is a step of dispersing a hydrophilic polymer and the particle 102 having the pores 102a to capture uremic toxins in a solvent and preparing a dispersion liquid of the particle 102 and the polymer.

The solvent may be any solvent that can stably dissolve the hydrophilic polymer, and more specifically, hexafluoroisopropanol, a mixed solvent of isopropanol and water, and the like can be used. The mixing ratio of the solvent and water is set, for example, from 10:90 to 90:10 (v/v). Among these, the solvent is preferably hexafluoroisopropanol which can be used at room temperature.

The particle concentration is sufficient as long as the particles can be uniformly dispersed in the dispersion liquid. More specifically, the particle concentration is preferably from 0.1 wt % to 10 wt %. The particles to be dispersed in the solvent can be dispersed even more uniformly by conducting ultrasonic irradiation.

The polymer concentration may be a concentration enabling spinning by the electrospinning method described later and can be adjusted within a range of, for example, 1 wt % to 15 wt %. In particular, the dispersion liquid with a polymer concentration of 5 wt % to 8 wt % is suitably used since it is possible to spin fibers having an average diameter of nanometer order.

The blood purification membrane manufacturing step S2 is a step for producing a blood purification membrane by spinning yarns from the dispersion liquid through the electrospinning method and aggregating the yarns.

Figure 5:
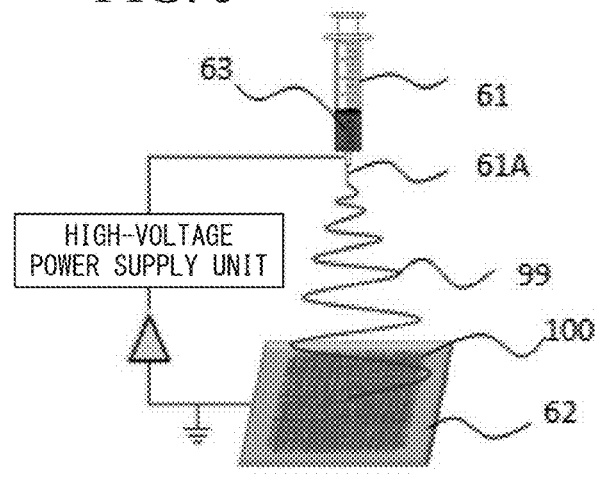
FIG. 5 is a schematic diagram showing an example of a method for manufacturing a blood purification membrane according to an embodiment of the present invention by an electrospinning method.

FIG. 5 is a schematic diagram showing an example of a method for manufacturing a blood purification membrane according to the present embodiment by the electrospinning method.

As shown in FIG. 5, while applying an electric field between a front end 61A of a syringe 61 filled with a dispersion liquid 63 and a metal plate 62, the dispersion liquid 63 is discharged from the front end 61A of the syringe 61 toward the metal plate 62 to produce the blood purification membrane 100.

<Form of Use of Dialysis Device (Dialyzer)>

Figure 6:
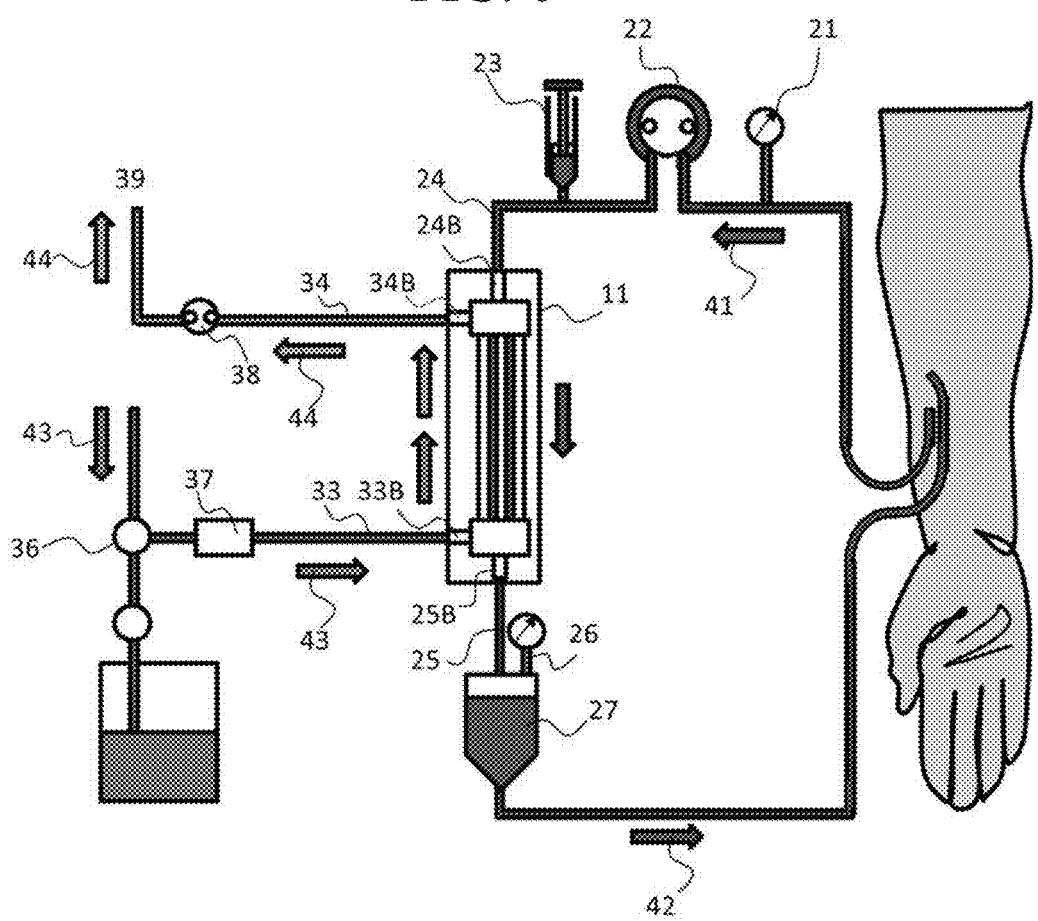
FIG. 6 is a schematic diagram showing an example of a form of use of a dialysis device according to the first embodiment of the present application.

FIG. 6 is a schematic diagram showing an example of a form of use of a dialysis device according to the present embodiment.

As shown in FIG. 6, a dialysis device 11 according to the present embodiment is mainly configured in such a manner that a tube 24 connected to a first tube joint portion 24B is connected to an artery, a tube 25 connected to a second tube joint portion 25B is connected to a vein, water is supplied from a tube 33 connected to a third tube joint portion 33B, and a dialysate is discharged from a tube 34 connected to a fourth tube joint portion 34B.

To the tube 24, an arterial pressure measurement device 21, a blood pump 22 and an anticoagulant addition device 23 are connected and blood 41 is supplied.

To the tube 25, an ultrasonic air detector 27 and a venous pressure measurement device 26 is connected, and blood 42 is discharged.

To the tube 33, a heater 37 and a concentration pump 36 are connected, and water 43 is supplied.

To the tube 34, a dialysate pump 38 is connected, and a dialysate 44 is discharged to a discharge unit 39.

<Dialysis Principle>

Figure 7A:
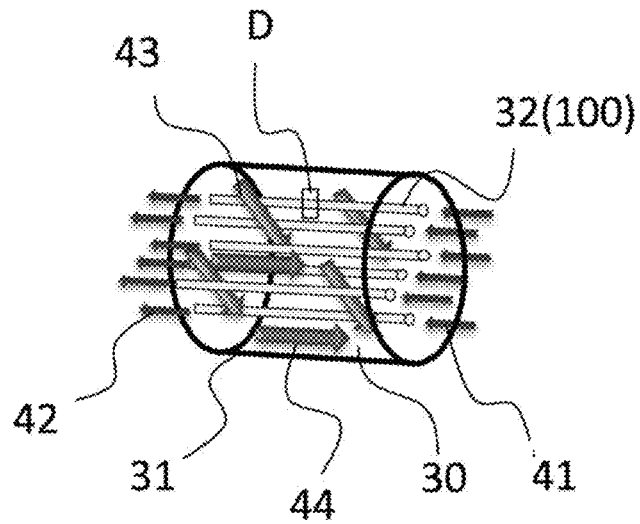
FIG. 7A is a perspective transparent view of the central portion of a dialysis device 11 in the use mode shown in FIG. 6.
Figure 7B:
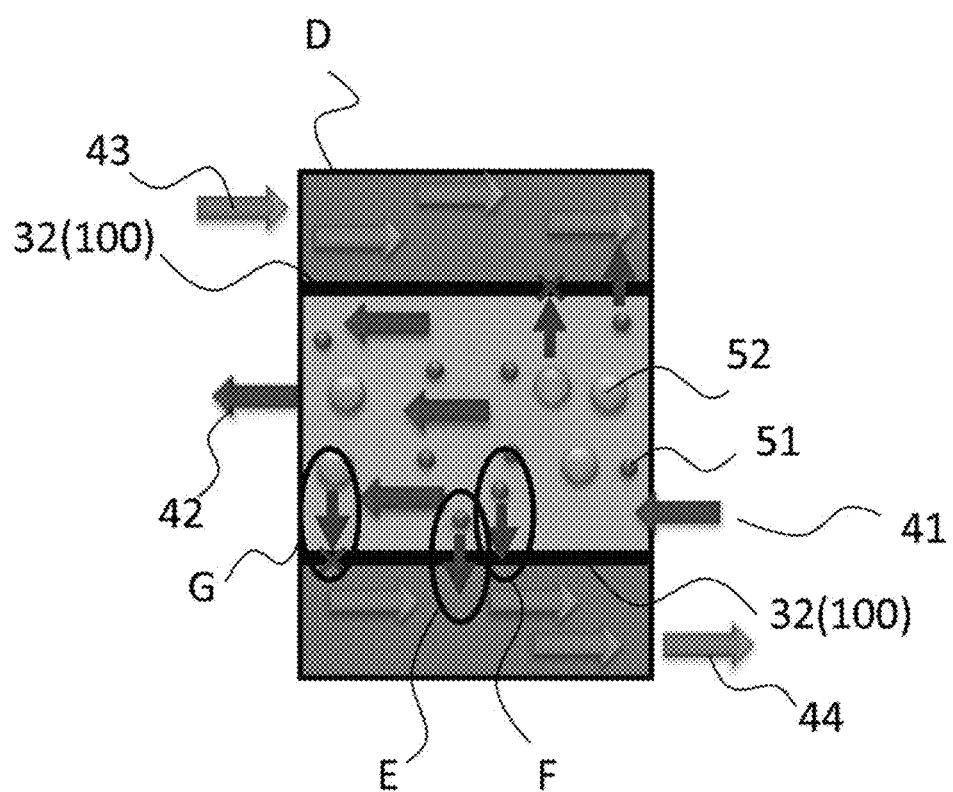
FIG. 7B is an enlarged view of a cross section along the axial direction of a portion D in FIG. 7A.

FIG. 7A is a perspective transparent view of the central portion of the dialysis device 11 in the form of use described above. FIG. 7B is an enlarged view of a cross section along the axial direction of a portion D in FIG. 7A.

As shown in FIG. 7A, through the central portion of the dialysis device 11, the blood 41 is supplied from one side, and the blood 42 is discharged. The water 43 is supplied from other side in a direction different from the direction in which the blood is supplied, and the water 44 is discharged only through a gap 30 between an inner surface 31b of the cylinder 31, and a plurality of thin cylinders 32.

In this case, as shown in FIG. 7B, a portion in which the blood passes and a portion in which water passes are separated by the blood purification membrane 100 of the thin cylinder 32.

As shown in a portion E in FIG. 7B, the blood purification membrane 100 is capable of discharging creatinine 51 which is a uremic toxin from the blood into water. In addition, as shown in a portion F in FIG. 7B, the blood purification membrane 100 is configured in such a manner that the uremic toxin creatinine 51 can be captured by the particles in the membrane. On the other hand, as shown in a portion G in FIG. 7B, the blood purification membrane 100 does not allow red blood cells 52 to pass through.

In this manner, it is possible to purify the blood by removing the uremic toxin creatinine from the blood 41, and to discharge the blood 42.

Second Embodiment

<Dialysis Device>

Next, a dialysis device according to a second embodiment of the present invention will be described.

Figure 8:
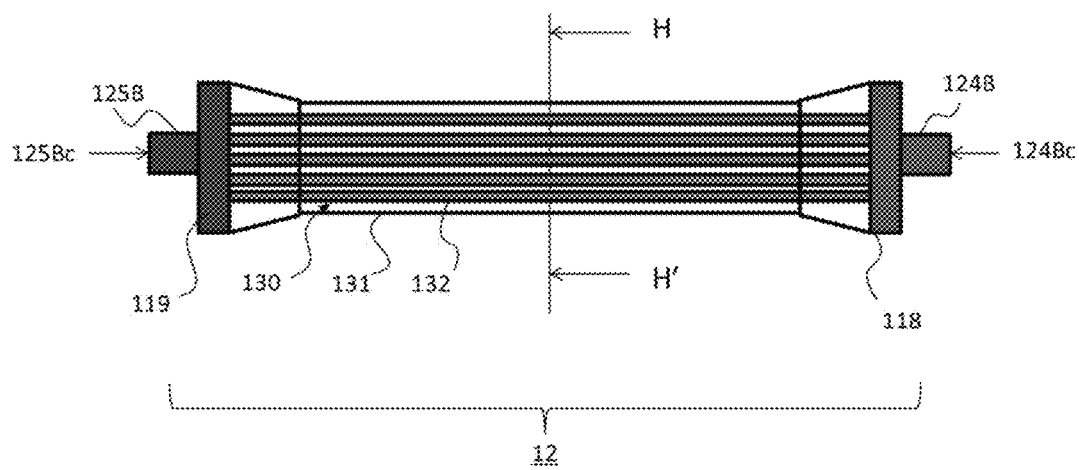
FIG. 8 is a schematic diagram showing a dialysis device according to a second embodiment of the present invention.
Figure 9A:
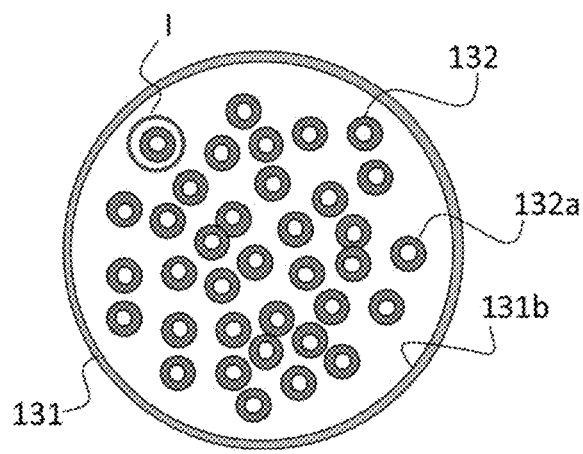
FIG. 9A is a cross sectional view taken along the line H-H' in FIG. 8.
Figure 9B:
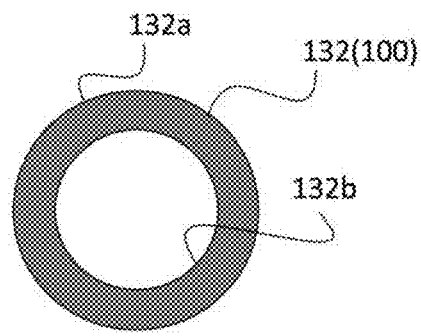
FIG. 9B is an enlarged view of a portion I in FIG. 8A.

FIG. 8 is a schematic diagram showing a dialysis device according to the present embodiment. FIG. 9A is a cross sectional view taken along the line H-H' in FIG. 8. FIG. 9B is an enlarged view of a portion I in FIG. 9A.

As shown in FIG. 8, a dialysis device 12 is mainly configured by including a cylinder 131, a plurality of thin cylinders 132, a first lid portion, and a second lid portion 119. The plurality of thin cylinders 132 are loaded in the cylinder 131 by aligning the axial direction. The first lid portion 118 closes the first end side of the cylinder 131, and the second lid portion 119 closes the second end (other end) side of the cylinder 131.

A first tube joint portion 124B is provided in the first lid portion 118, and a second tube joint portion 125B is provided in the second lid portion 119.

A first opening 124Bc of the first tube joint portion 124B is in communication with a second opening 125Bc of the second tube joint portion 125B only through the inside of the plurality of thin cylinders 132 (not shown).

In addition, a gap 130 is provided between the inner surface of the cylinder 131 and the outer surface of the plurality of thin cylinders 132.

In the present embodiment, as shown in FIG. 9A, 38 thin cylinders 132 are placed in a single cylinder 131. However, the number of the thin cylinders 132 inserted into the cylinder 131 is not limited thereto.

As shown in FIG. 9B, the thin cylinders 132 are cylinders having an outer surface 132a and an inner surface 132b. However, the shape of the thin cylinders 132 is not limited thereto, and may be formed into a polygonal shape.

As shown in FIG. 9B, the thin cylinders 132 are formed by the blood purification membrane 100 according to the present embodiment in such a manner that the membrane thickness is thicker, as compared with the first embodiment. As a result, all of uremic toxins can be captured within the particles in the membrane, and the membrane can be used without causing water to flow through.

Third Embodiment

<Dialysis Device>

Next, a dialysis device according to a third embodiment of the present invention will be described.

Figure 10A:
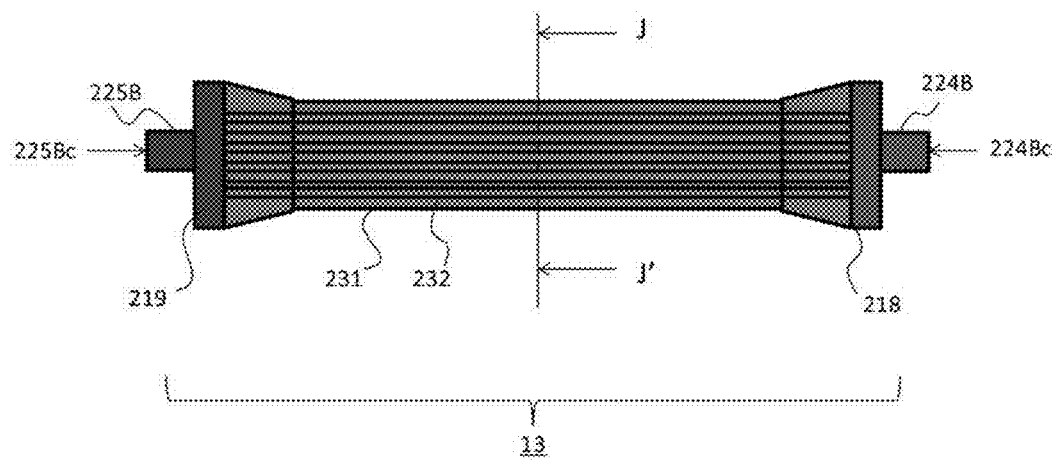
FIG. 10A is a front view showing an outline of a dialysis device according to a third embodiment of the present invention.
Figure 10B:
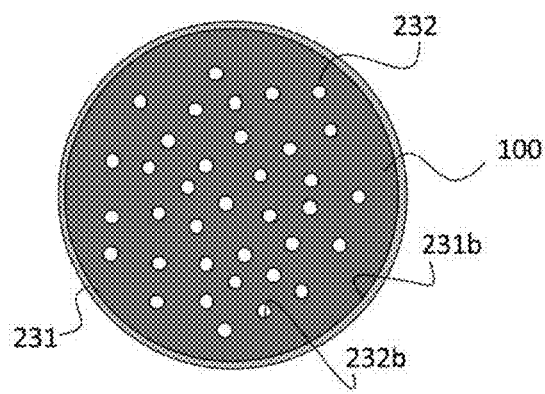
FIG. 10B is an enlarged view of a cross section taken along the line in FIG. 10A.

FIG. 10A is a front schematic view showing a dialysis device 13 according to the present embodiment. FIG. 10B is an enlarged view of a cross section taken along the line J-J' in FIG. 10A.

As shown in FIG. 10A, a dialysis device 13 is mainly configured by including a cylinder 231, a plurality of thin cylindrical portions 232, a first lid portion 218, and a second lid portion 219. The plurality of thin cylindrical portions 232 are loaded in the cylinder 231 by aligning the axial direction. The first lid portion 218 closes the first end side of the cylinder 231. The second lid portion 219 closes the second end (other end) side of the cylinder 231.

A first tube joint portion 224B is provided in the first lid portion 218, and a second tube joint portion 225B is provided in the second lid portion 219.

An opening 224Bc of the first tube joint portion 224B is in communication with an opening 225Bc of the second tube joint portion 225B only through the inside of the plurality of thin cylindrical portions 232 (not shown).

As shown in FIG. 10B, the thin cylindrical portions 232 are constituted only by pores, and the blood purification membrane 100 is filled between an inner surface 232b of the thin cylindrical portions 232 and an inner surface 231b of the cylinder 231.

As a result, all of uremic toxins can be captured within the particles in the membrane, and the membrane can be used without causing water to flow through.

The blood purification membrane according to the above embodiment is a blood purification membrane capable of adsorbing creatinine which is a uremic toxin in the blood and purifying the blood, and is configured to include fibers and particles adhered to the aforementioned fibers, wherein the aforementioned fibers are composed of a polymer insoluble in water, the aforementioned particles contain $SiO_2$ and $Al_2O_3$, and pores capable of incorporating at least a portion of the aforementioned uremic toxin are provided in the aforementioned particles. Therefore, it is possible to rapidly adsorb the uremic toxin creatinine in the blood and to produce fibers exhibiting excellent blood compatibility.

Since the blood purification membrane according to the above embodiment is configured in such a manner that an $SiO_2/Al_2O_3$ ratio of the aforementioned particles is equal to or more than 18 and equal to or less than 240, it is possible to quickly adsorb the uremic toxin creatinine and to produce fibers exhibiting excellent blood compatibility.

Since the blood purification membrane according to the above embodiment is configured in such a manner that the aforementioned particle is zeolite or a zeolite composite, it is possible to quickly adsorb the uremic toxin creatinine and to produce fibers exhibiting excellent blood compatibility.

Since the blood purification membrane according to the above embodiment is configured in such a manner that the aforementioned particles are particles having a maximum diameter of equal to or less than 5 μm, it is possible to uniformly disperse in the fibers, quickly adsorb the uremic toxin creatinine and to produce fibers exhibiting excellent blood compatibility.

Since the blood purification membrane according to the above embodiment is configured in such a manner that the aforementioned hydrophilic polymer is any one selected from the group consisting of an ethylene-vinyl alcohol copolymer (EVAL), polyvinylpyrrolidone (PVP), polyhydroxyethyl methacrylate (PHEMA), and polyvinyl alcohol (PVA), it is possible to quickly adsorb the uremic toxin creatinine and to produce fibers exhibiting excellent blood compatibility.

Since the blood purification membrane according to the above embodiment is configured in such a manner that a diameter of the aforementioned fiber is equal to or greater than 100 nm and equal to or less than 1,000 nm, it is possible to quickly adsorb the uremic toxin creatinine and to produce fibers exhibiting excellent blood compatibility.

Since the blood purification membrane according to the above embodiment is configured to have a thickness of equal to or more than 10 nm, it is possible to quickly adsorb the uremic toxin creatinine and to produce fibers exhibiting excellent blood compatibility.

Since the blood purification membrane according to the above embodiment has a configuration in which the aforementioned particles are fixed to the polymer, it is possible to quickly adsorb the uremic toxin creatinine and to produce fibers exhibiting excellent blood compatibility.

Since the method for manufacturing a blood purification membrane according to the above embodiment is configured to include: a step of dispersing a hydrophilic polymer and particles including $SiO_2$ and $Al_2O_3$ and provided with pores capable of incorporating at least a portion of creatinine serving as a uremic toxin, in a solvent, thereby preparing a dispersion liquid of the particles and the hydrophilic polymer; and a step of producing a blood purification membrane by spinning a yarn from the aforementioned dispersion liquid through an electrospinning method and coagulating the yarn, the blood purification membrane capable of adsorbing creatinine as a uremic toxin in the blood and purifying the blood, which includes fibers and particles adhered to the aforementioned fibers, wherein the aforementioned fibers include a polymer insoluble in water, the aforementioned particles contain $SiO_2$ and $Al_2O_3$, and the aforementioned particles are provided with pores capable of incorporating at least a portion of the aforementioned uremic toxin, fibers quickly adsorbing uremic toxins and exhibiting excellent blood compatibility can be easily produced within a short period of time.

Since the dialysis device according to the above embodiment is configured to include: a cylinder, a plurality of thin cylinders filled inside the aforementioned cylinder by aligning the axial direction, a lid portion for closing one end side of the aforementioned cylinder, another lid portion for closing the other end side of the aforementioned cylinder, a first tube joint portion provided in the aforementioned lid portion, and a second tube joint portion provided in the aforementioned another lid portion, the dialysis device in which an opening of the aforementioned first tube joint portion is in communication with an opening of the aforementioned second tube joint portion only through the aforementioned plurality of thin cylinders, and the aforementioned thin cylinder is formed by the blood purification membrane described earlier, it is possible to quickly adsorb uremic toxins and remove uremic toxins from the body without requiring a large amount of water by circulating blood inside the plurality of thin cylinders. For this reason, it can be used for an emergency treatment of acute uremia even in sparsely populated areas that are not equipped with sufficient infrastructure, and even in times of emergency where lifelines have been cut off.

Since the dialysis device according to the above embodiment is configured to further include: a third tube joint portion provided in the aforementioned cylinder, and a fourth tube joint portion provided in the aforementioned cylinder, in which an opening of the aforementioned third tube joint portion is in communication with an opening of the aforementioned fourth tube joint portion only through a gap between the inner surface of the aforementioned cylinder and the outer surface of the aforementioned plurality of thin cylinders, it is possible to quickly adsorb uremic toxins and to remove uremic toxins from the body, and the dialysis device can be used for the treatment of acute uremia, by circulating water through the gap between the inner surface of the cylinder and the outer surface of the thin cylinder and circulating the blood inside the plurality of thin cylinders.

Since the dialysis device according to the above embodiment is configured to include: a cylinder, a plurality of thin cylindrical portions formed inside the aforementioned cylinder by aligning the axial direction, a lid portion for closing one end side of the aforementioned cylinder, another lid portion for closing the other end side of the aforementioned cylinder, a first tube joint portion provided in the aforementioned lid portion, and a second tube joint portion provided in the aforementioned another lid portion, the dialysis device in which an opening of the aforementioned first tube joint portion is in communication with an opening of the aforementioned second tube joint portion only through the inside of the aforementioned plurality of thin cylindrical portions, and the blood purification membrane described earlier is filled between the aforementioned cylinder and the afore- Next, the eight types of zeolite particles were immersed for 5 hours in 5 ml of the aqueous creatinine solutions to prepare 8 types of evaluation solutions.

Then, using a UV-VIS spectrometer, changes in the light absorption intensity of the eight types of evaluation solutions at a peak wavelength of 233 nm were measured. As a result, creatinine adsorption properties of the eight types of zeolite particles (Test Examples 1-1 to 1-8) were evaluated.

Figure 11:
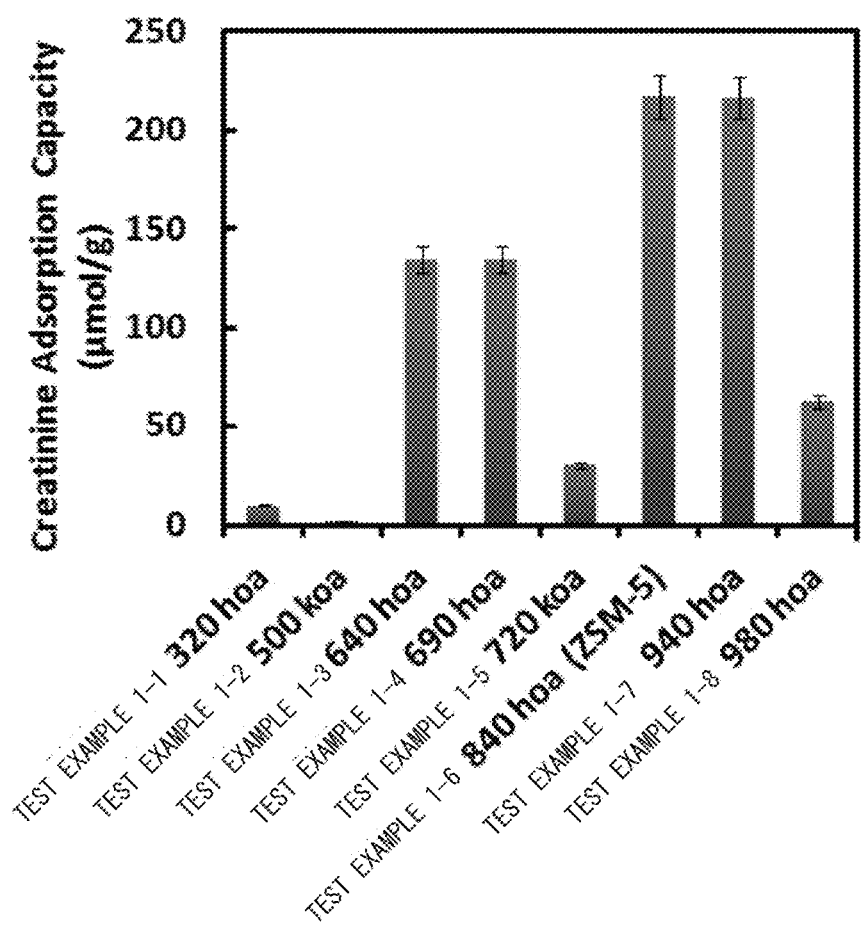
FIG. 11 is a graph showing the evaluation results of the creatinine adsorption properties of eight types of zeolite particles (Test Examples 1-1 to 1-8).

FIG. 11 is a graph showing the evaluation results of the creatinine adsorption properties of eight types of zeolite particles (Test Examples 1-1 to 1-8). Table 1 is a table showing the conditions and results thereof.

TABLE 1

|  |  |  | Pore diameter (nm) | Pore size ($nm^2$) | $SiO_2/Al_2O_3$ (mol/mol) | Amount of creatinine adsorption (μmol/g) |
|---|---|---|---|---|---|---|
| Test Example 1-1 | HSZ-320HOA | Y type | 0.56 × 0.56 | 0.31 | 5.5 | 10 |
| Test Example 1-2 | HSZ-500KOA | L type | 0.71 × 0.71 | 0.5 | 6.1 | 0 |
| Test Example 1-3 | HSZ-640HOA | Mordenite type | 0.65 × 0.70<br>0.34 × 0.48 | 0.46<br>0.16 | 18 | 130 |
| Test Example 1-4 | HSZ-690HOA | Mordenite type | 0.65 × 0.70<br>0.34 × 0.48 | 0.46<br>0.16 | 240 | 130 |
| Test Example 1-5 | HSZ-720KOA | Ferrierite type | 0.42 × 0.54<br>0.35 × 0.48 | 0.23<br>0.17 | 18 | 30 |
| Test Example 1-6 | HSZ-840HOA | ZSM-5 | 0.51 × 0.55<br>0.53 × 0.56 | 0.28<br>0.3 | 38 | 220 |
| Test Example 1-7 | HSZ-940HOA | Beta type | 0.66 × 0.67<br>0.56 × 0.56 | 0.44<br>0.31 | 37 | 220 |
| Test Example 1-8 | HSZ-980HOA | Beta type | 0.66 × 0.67<br>0.56 × 0.56 | 0.44<br>0.31 | 500 | 50 | mentioned plurality of thin cylindrical portions, it is possible to quickly adsorb uremic toxins and remove uremic toxins from the body without requiring a large amount of water. For this reason, it can be used for an emergency treatment of acute uremia even in sparsely populated areas that are not equipped with sufficient infrastructure, and even in times of emergency where lifelines have been cut off.

The blood purification membrane, method for manufacturing a blood purification membrane, and dialysis device according to the above embodiments are not limited to the above embodiments, and can be implemented with various modifications within the technical scope of the present invention. Specific examples of the present embodiment are shown by the following examples. However, the present invention is in no way limited by these examples.

EXAMPLES

Test Example 1

<Evaluation of Toxin Adsorption Properties of 8 Types of Zeolites>

First, 8 types of zeolite particles were prepared (manufactured by Tosoh Corporation). Physical property values of these zeolites have been made available to the public on the website of Japan Association of zeolite and the like, in addition to the manufacturer's website.

Next, as a uremic toxin, creatinine (Mw=113, x=0.71 nm, y=0.81 nm, z=0.30 nm, manufactured by Wako Pure Chemical Industries, Ltd.) which was a metabolic product of proteins was prepared. Then, creatinine was dissolved in water to prepare a 191 μM aqueous solution of creatinine.

ZSM-5 (HSZ-840HOA) and a beta-type zeolite (pore: 0.66×0.67 nm, HSZ-940HOA, manufactured by Tosoh Corporation) having pores with substantially the same size as that of creatinine (0.71×0.80×0.30 nm) adsorbed creatinine the most (220 μmol/g).

From this result, it became clear that the creatinine adsorption characteristics of the zeolites depended on the pore size and hydrophilicity/hydrophobicity ($SiO_2/Al_2O_3$ molar ratio) of the zeolites.

More specifically, it became clear that the size of the pores of the zeolite was at least 1.39 times, but not more than 2.14 times, as large as the area of the smallest surface of the smallest rectangular parallelepiped enclosing creatinine, and that the amount of creatinine adsorption became as high as 130 (μmol/g) or more when the $SiO_2/Al_2O_3$ molar ratio of the zeolite was 18 or more and 240 or less.

Test Example 2

<Fiber Preparation>

First, as a polymer to serve as a base of the fiber, an ethylene-vinyl alcohol copolymer (EVOH) (EVAL-E105B, ethylene ratio: 44%, manufactured by Kuraray Co., Ltd.) which was insoluble in water while being hydrophilic and required no crosslinking after the membrane formation was prepared. This ethylene-vinyl alcohol copolymer exhibits excellent blood compatibility (blood cell inactivation, coagulation system inactivation), and there are proven medical applications.

Next, EVAL was dissolved in a solvent at a predetermined concentration, and then subjected to ultrasonic mixing, thereby preparing a solution for spinning.

As a solvent, a mixed solution of isopropanol and water or hexafluoroisopropanol (HFIP) was used. HFIP was prepared at normal temperature, and the mixed solution of isopropanol and water was prepared at 70° C. with a volume ratio of 70:30.

The polymer concentration was set to any one of 5 wt %, 6 wt %, 7 wt %, 8.5 wt %, and 10 wt %.

Next, using the electrospinning method, fibers were spun from the solution for spinning.

The type of solvent, the polymer concentration, the electric voltage, and the ejection rate which were parameters at the time of electrospinning were adjusted. The electric voltage was set to 25 kV, and the ejection rate was set to 1 ml/h.

Figure 12:
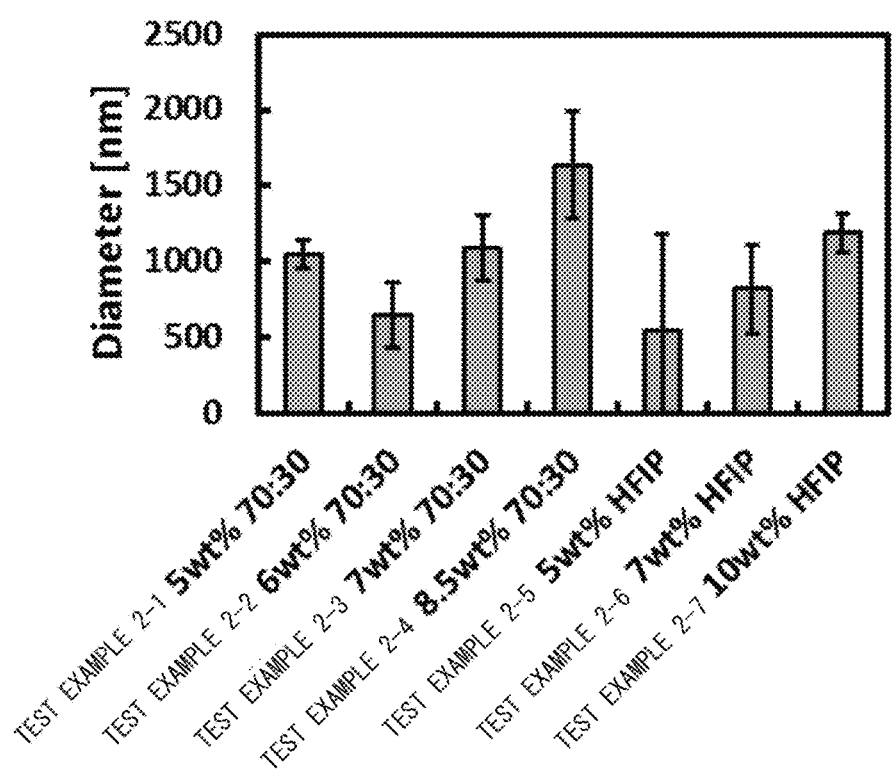
FIG. 12 is a graph showing the relationship between the conditions of a dispersion liquid and the generation fiber diameter.

As a result, it was possible to spin EVAL fibers of various diameters (400 to 1,000 nm) (Test Examples 2-1 to 2-7). FIG. 12 is a graph showing the relationship between the conditions of the dispersion liquid (shown on the horizontal axis of the graph) and the diameters of the generated fibers (shown on the vertical axis of the graph). Table 2 is a table showing the experimental conditions and results. It should be noted that the average diameter values of the fibers do not include the size of the beads.

Then, EVAL and HSZ-940HOA were subjected to ultrasonic mixing with hexafluoroisopropanol at a ratio of the polymer concentration of 7 wt % and the zeolite concentration of 0.7 wt %, thereby preparing a dispersion solution.

Next, using the electrospinning method, zeolite particle-containing fibers were spun from the dispersion solution.

Parameters at the time of electrospinning were set so that the electric voltage was 25 kV, and the ejection rate was 1 ml/h.

Example 1-2

<Preparation of Zeolite Particle-Containing Fiber>

An attempt was made to produce fibers of Example 1-2 in the same manner as in Example 1, with the exception that a dispersion solution was prepared at a ratio of the polymer concentration of 7 wt % and the zeolite concentration of 0.35 wt %. It was possible to produce particle-containing fibers.

As described above, in those cases where zeolite of 0.3 to 0.7 wt % (10 wt % with respect to the fiber) was ultrasonically mixed with the polymer solution at the time of spinning (EVOH/HFIP: 7 wt %), it was possible to spin the fiber internally capturing zeolite with good reproducibility. The

TABLE 2

| | Type of polymer | Polymer concentration wt % | Type of solvent | Fiber average diameter nm | Presence of beads | Ease of handling | Overall evaluation |
|---|---|---|---|---|---|---|---|
| Test Example 2-1 | EVAL | 5 | Mixed solvent of water/isopropanol | 1,000 | ○ | ○ | |
| Test Example 2-2 | EVAL | 6 | Mixed solvent of water/isopropanol | 700 | ○ | Δ | |
| Test Example 2-3 | EVAL | 7 | Mixed solvent of water/isopropanol | 1,000 | x | ○ | |
| Test Example 2-4 | EVAL | 8.5 | Mixed solvent of water/isopropanol | 1,550 | x | ○ | |
| Test Example 2-5 | EVAL | 5 | HFIP | 480 | x | x | |
| Test Example 2-6 | EVAL | 7 | HFIP | 800 | x | ○ | ○ |
| Test Example 2-7 | EVAL | 10 | HFIP | 1,080 | x | ○ | |

Morphology of the fibers was evaluated by SEM (scanning electron microscope) images. Beads were observed, in addition to the fibers, in Test Examples 2-1 and 2-2. Variations in the fiber diameter were large, and it was impossible to produce membranes with good reproducibility in Test Example 2-5. It was possible to produce membranes using the fibers with good reproducibility in Test Examples 2-2, 2-3, 2-4, 2-6, and 2-7. In addition, membranes were easily torn and difficult to handle in Test Examples 2-2 and 2-5.

When evaluated in terms of the morphology, the handling ease of the membrane produced, and the membrane formation conditions, the fibers produced under the condition of EVOH/HFIP of 7 wt % were optimal, because the average diameter was small and the membrane could be formed with good reproducibility.

Example 1-1

<Preparation of Zeolite Particle-Containing Fiber Composite Membrane>

First, zeolite particles HSZ-940HOA (manufactured by Tosoh Corporation) were prepared.

Then, as a polymer to serve as a base of the fiber, an ethylene-vinyl alcohol copolymer (EVOH) (EVAL-E105B, ethylene ratio: 44%, manufactured by Kuraray Co., Ltd.) was prepared.

zeolite content in the fibers was measured by using a simultaneous thermogravimetric/differential thermal analyzer.

Comparative Example 1-1

<Preparation of Zeolite Particle-Containing Fiber>

An attempt was made to produce fibers of Comparative Example 1-1 in the same manner as in Example 1, with the exception that a dispersion solution was prepared at a ratio of the polymer concentration of 7 wt % and the zeolite concentration of 1.4 wt %.

Although it was possible to produce particle-containing fibers, the zeolite content in the fibers was substantially the same as in Example 1-1.

Comparative Example 1-2

<Preparation of Zeolite Particle-Containing Fiber>

An attempt was made to produce fibers of Comparative Example 1-2 in the same manner as in Example 1, with the exception that a dispersion solution was prepared at a ratio of the polymer concentration of 7 wt % and the zeolite concentration of 2.1 wt %.

However, it was not possible to produce particle-containing fibers.

As described above, when the mixing ratio was 30 wt % or more, it was not possible to obtain fibers.

It is thought that this is because when zeolite was mixed at a predetermined concentration or more, the size of the aggregates increased during spinning since zeolite particles having an average particle diameter of 2.4 µm were used.

Comparative Example 1-3

<Preparation of Zeolite Particle-Containing Fiber>

An attempt was made to produce fibers of Comparative Example 1-3 in the same manner as in Example 1, with the exception that zeolite particles were not mixed. It was possible to produce fibers.

The experimental conditions and results of Examples and Comparative Examples described above are shown in Table 3.

Figure 16:
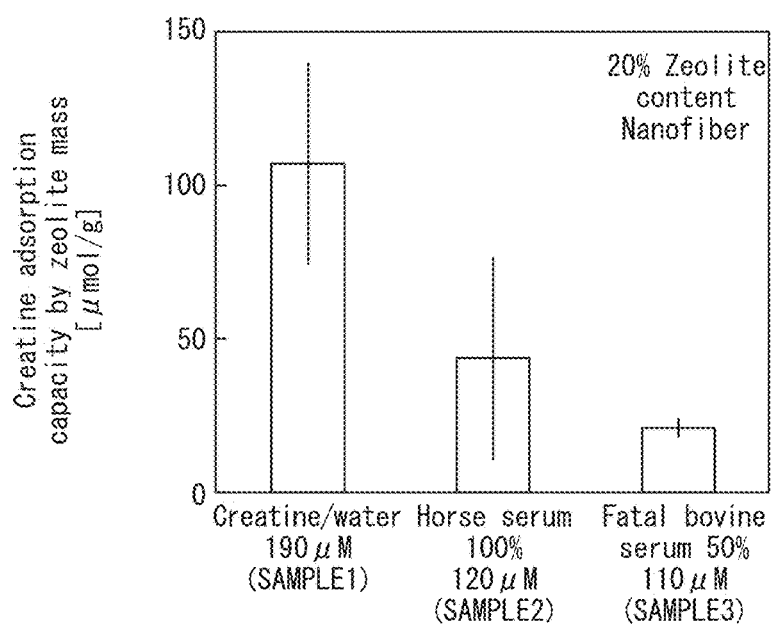
FIG. 16 is a graph showing the evaluation results of the creatinine adsorption properties.

FIG. 16 is a graph comparing the amount of creatinine adsorption (weight) of samples 1 to 3. A mixture solution of creatinine and water (creatinine content: 190 micromoles) was prepared as the sample 1, and a solution obtained by containing horse serum in the sample 1 (creatinine content: 120 micromoles), and a solution obtained by containing fetal bovine serum in the sample 1 (creatinine content: 110 micromoles) were prepared as the sample 2 and the sample 3, respectively. Each of the samples 1 to 3 was allowed to pass through the blood purification membrane using fibers containing 20% of zeolite particles. As shown in FIG. 16, it became clear that it was possible to adsorb creatinine to some extent, although the amount of creatinine adsorption was reduced, under the condition in which horse serum or fetal bovine serum was contained.

Although the embodiments of the present invention have been described in detail with reference to the drawings,

TABLE 3

| | Type of zeolite | Zeolite average particle diameter µm | Zeolite concentration wt % | Pore diameter nm | Mixing ratio of zeolite relative to polymer wt % | Type of polymer | Polymer concentration wt % | Type of solvent | Membrane | Content ratio of zeolite relative to fiber weight wt % | Amount of creatinine adsorption µmol/g | Overall evaluation |
|---|---|---|---|---|---|---|---|---|---|---|---|---|
| Example 1-1 | HSZ-940HOA | 2.4 | 0.7 | 0.66 × 0.67 | 10 | EVAL | 7 | HFIP | Production succeeded | 8 | 12 | ○ |
| Example 1-2 | | | 0.35 | 0.56 × 0.56 | 5 | | | | Production succeeded | 3 | 2 | Δ |
| Comparative Example 1-1 | | | 1.4 | | 20 | | | | Production succeeded | 10 | 13 | Δ |
| Comparative Example 1-2 | | | 2.1 | | 30 | | | | Production failed | — | — | x |
| Comparative Example 1-3 | — | — | 0 | — | 0 | | | | Production succeeded | 0 | 0 | x |

Figure 13:
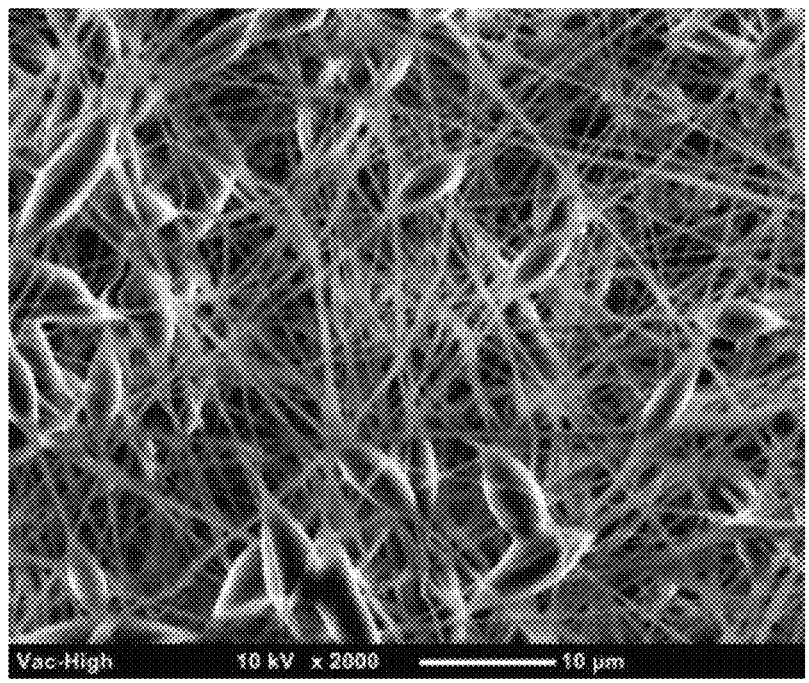
FIG. 13 is an SEM image of the fibers (membrane) of Example 1-1.

FIG. 13 is an SEM image or the fibers of Example 1-1. As shown in FIG. 13, the fibers internally incorporating zeolite particles were spun. It should be noted that the aggregates (about 5 µm×10 µm) were confirmed to be composed of zeolite from the results of EDX mapping.

Figure 14:
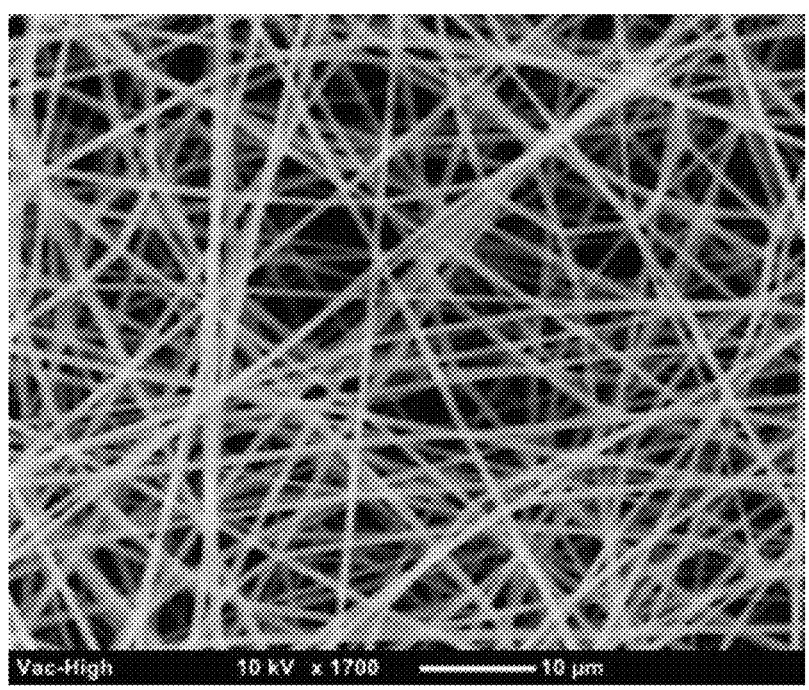
FIG. 14 is an SEM image of the fibers (membrane) of Comparative Example 1-3.

FIG. 14 is an SEM image of the fibers of Comparative Example 1-3. It was possible to form a membrane composed of EVAL fibers by the electrospinning method using a dispersion liquid with a polymer concentration of 7 wt %.

<Evaluation of Uremic Toxin Adsorption Properties>

First, as a uremic toxin, creatinine (Mw=113, x=0.71 nm, y=0.81 nm, z=0.30 nm) which was a metabolic product of proteins was prepared.

Then, creatinine was dissolved in water to prepare a 190 µM aqueous solution of creatinine. Using this aqueous creatinine solution, the creatinine adsorption/removal properties of fibers were evaluated in an aqueous solution system.

Then, the fibers were immersed for 5 hours in 5 ml of the aqueous creatinine solutions, and then changes in the light absorption intensity at a peak wavelength of 233 nm were measured using a UV-VIS spectrometer, to evaluate the creatinine adsorption properties of the fibers.

Figure 15:
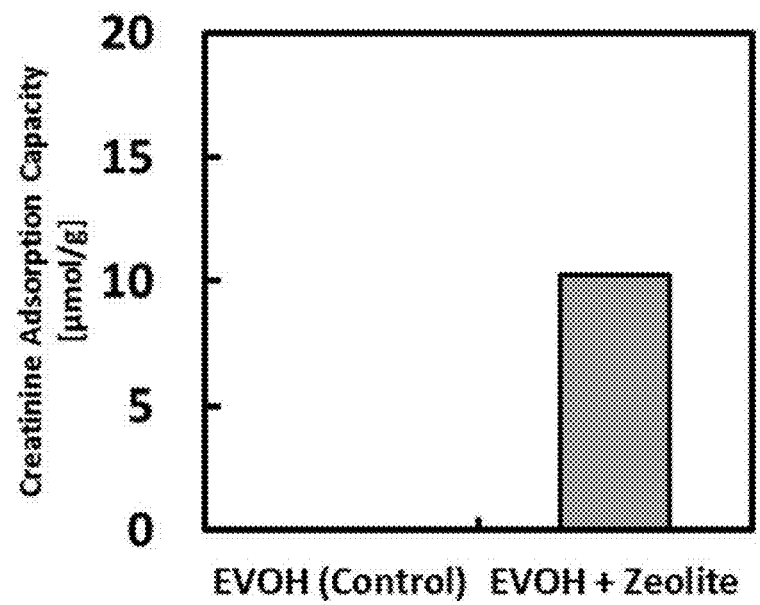
FIG. 15 is a graph showing the evaluation results of the creatinine adsorption properties of the fibers (membrane) of Example 1 and the fibers (membrane) of Comparative Example 1-3.

FIG. 15 is a graph showing the evaluation results of the creatinine adsorption properties of the fibers (membrane) of Example 1-1 and the fibers (membrane) of Comparative Example 1-3. It was possible to remove 12 µmol/g (fiber) of creatinine by the fibers (membrane) of Example 1-1. On the other hand, it was not possible to remove creatinine by the fibers (membrane) of Comparative Example 1-3.

specific configurations are not limited to these embodiments, and other designs and the like without departing from the spirit and scope of the present invention are also included.

INDUSTRIAL APPLICABILITY

According to the blood purification membrane, method for manufacturing a blood purification membrane and dialysis device described above, it is possible to quickly adsorb creatinine as a uremic toxin, achieve excellent blood compatibility, and to remove uremic toxins from the body without requiring a large amount of water. Therefore, they may become novel medical materials that can be used for an emergency treatment of acute uremia by adsorbing and removing creatinine, even in sparsely populated areas that are not equipped with sufficient infrastructure, and even in times of emergency where lifelines have been cut off, and can be utilized in the manufacturing industry to produce novel medical materials and in the dialysis device industry.

REFERENCE SIGNS LIST 11, 12, 13: Dialysis device;
18, 118, 218: First lid portion;
19, 119, 219: Second lid portion;
24B, 124B, 224B: First tube joint portion;
24Bc, 124Bc, 224Bc: Opening of first tube joint portion;
25B, 125B: Second tube joint portion;
25Bc, 125Bc, 225Bc: Opening of second tube joint portion;
30, 130: Gap;

31, 131, 231: Cylinder;
31b, 131b, 231b: Inner surface;
32, 132: Thin cylinder;
32a, 132a: Outer surface;
33B: Third tube joint portion;
34B: Fourth tube joint portion;
33Bc: Opening of third tube joint portion;
34Bc: Opening of fourth tube joint portion;
100: Blood purification membrane;
101: Fiber;
102: Particle;
102a: Pore;
232: Thin cylindrical portion (thin cylinder)

The invention claimed is:

1. A blood purification membrane capable of adsorbing creatinine which is a uremic toxin in the blood and purifying the blood, the blood purification membrane comprising:
fibers; and
one or more particles adhered to said fibers,
wherein said fibers comprise a hydrophilic polymer insoluble in water,
wherein each of said one or more particles include zeolite or zeolite composite, said zeolite or zeolite composite contains $SiO_2$ and $Al_2O_3$,
wherein pores capable of incorporating at least a portion of said uremic toxin are provided in each of said one or more particles,
wherein a size of said pores is at least 1.39 times, but not more than 2.14 times, as large as an area of a smallest surface of a smallest rectangular parallelepiped enclosing said uremic toxin in a form of creatinine,
wherein said blood purification membrane is a mesh-like aggregation of said fibers having a plurality of mesh pores that allow said uremic toxin to move in said blood purification membrane, and
wherein said one or more particles are incorporated into said fibers.

2. The blood purification membrane according to claim 1, wherein an $SiO_2/Al_2O_3$ molar ratio of each of said one or more particles is equal to or more than 18 and equal to or less than 240.

3. The blood purification membrane according to claim 1, wherein each of said one or more particles is a particle having a maximum diameter of 5 μm or less.

4. The blood purification membrane according to claim 1, wherein said hydrophilic polymer is any one selected from the group consisting of polyvinylpyrrolidone (PVP), polyhydroxyethyl methacrylate (PHEMA), and polyvinyl alcohol (PVA) to each of which an insolubilization treatment has been performed, and an ethylene-vinyl alcohol copolymer (EVAL).

5. The blood purification membrane according to claim 1, wherein a diameter of said fibers is at least 100 nm and not more than 1,000 nm.

6. The blood purification membrane according to claim 1, wherein each of said one or more particles is fixed to said polymer while a surface of each of said one or more particles is coated with said polymer.

7. A method for manufacturing a blood purification membrane according to claim 1, the method comprising:
a step of dispersing a hydrophilic polymer and particles including $SiO_2$ and $Al_2O_3$ and provided with pores capable of incorporating at least a portion of creatinine which is a uremic toxin, in a solvent, thereby preparing a dispersion liquid of the particles and the hydrophilic polymer; and
a step of producing the blood purification membrane by spinning fibers from said dispersion liquid through an electrospinning method and coagulating said fibers,
the blood purification membrane capable of adsorbing creatinine as a uremic toxin in the blood and purifying the blood, which comprises fibers and particles adhered to said fibers,
wherein said fibers comprise a polymer insoluble in water, said particles include $SiO_2$ and $Al_2O_3$, and said particles are provided with pores capable of incorporating at least a portion of said uremic toxin.

8. A dialysis device comprising:
a cylinder;
a plurality of thin cylinders filled inside said cylinder by aligning the axial direction;
a first lid portion for closing a first end side of said cylinder;
a second lid portion for closing a second end side of said cylinder;
a first tube joint portion provided in said first lid portion; and
a second tube joint portion provided in said second lid portion,
wherein an opening of said first tube joint portion is in communication with an opening of said second tube joint portion only through the inside of said plurality of thin cylinders, and
said thin cylinders are formed by the blood purification membrane according to claim 1.

9. The dialysis device according to claim 8, further comprising:
a third tube joint portion provided in said cylinder; and
a fourth tube joint portion provided in said cylinder,
wherein an opening of said third tube joint portion is in communication with an opening of said fourth tube joint portion only through a gap between an inner surface of said cylinder and an outer surface of said plurality of thin cylinders.

10. A dialysis device comprising:
a cylinder;
a plurality of thin cylindrical portions formed inside said cylinder by aligning the axial direction;
a first lid portion for closing a first end side of said cylinder;
a second lid portion for closing a second end side of said cylinder;
a first tube joint portion provided in said first lid portion; and
a second tube joint portion provided in said second lid portion,
wherein an opening of said first tube joint portion is in communication with an opening of said second tube joint portion only through the inside of said plurality of thin cylindrical portions, and
the blood purification membrane according to claim 1 is filled between said cylinder and said plurality of thin cylindrical portions.

11. The blood purification membrane according to claim 1, wherein said zeolite is one or more selected from a group consisting of a beta type zeolite, a mordenite type zeolite, and a ZSM-5.

12. The blood purification membrane according to claim 1, wherein said blood purification membrane is in a form of a cylinder.

* * * * *